United States Patent [19]

van Andel

[11] Patent Number: Plant 5,498

[45] Date of Patent: Jun. 25, 1985

[54] CARNATION NAMED STANPIRAN

[75] Inventor: Jacob van Andel, Aalsmeer, Netherlands

[73] Assignee: B. V. Handelskwekerij, M. C. van Staaveren, Aalsmeer, Netherlands

[21] Appl. No.: 556,682

[22] Filed: Nov. 30, 1983

[51] Int. Cl.[3] ..... A01H 5/00

[52] U.S. Cl. ..... Plt./73

[58] Field of Search ..... Plt./73, 70

*Primary Examiner*—Robert E. Bagwill

*Attorney, Agent, or Firm*—Charles W. Rummler

[57] ABSTRACT

A new variety of carnation plant distinguished by the orange red coloring of its relatively large blooms which are borne on strong, upright flower stems and by its continuous production of flowers which retain the same coloration in all seasons of blooming.

1 Drawing Figure

BACKGROUND OF THE NEW PLANT

This new carnation cultivar originated at Aalsmeer, Holland, as a sport of an unpatented carnation variety named "Doranja" and was discovered by me in 1977. I selected this sport for propagation because of its relatively large size and unusual coloration. Propagation of this discovery flower was done by means of cuttings and the success of that propagation led me to continue propagating this new plant through successive generations at Aalsmeer, which demonstrated that the new plant not only retained the continuous production of blooms and distinctive coloration but also that its distinguishing characteristics held true from generation to generation and appeared to be firmly fixed.

DESCRIPTION OF THE DRAWING

My new carnation cultivar is illustrated by the accompanying full color photographic drawing which shows a three-quarter view of a fully developed bloom and partial face views of the blooms which show their general form and coloration, the colors shown being as nearly true as it is possible to obtain by conventional photographic procedures.

DESCRIPTION OF THE NEW PLANT

The following is a detailed description of my new carnation cultivar based upon observation of plants grown under conventional greenhouse procedures at Aalsmeer, Holland, the color designations being according to The R.H.S. Colour Chart published by The Royal Horticultural Society of London, England.

THE PLANT

Origin: Sport.
Parentage: The variety "Doranja" (unpatented).
Classification:
- *Botanic.*—Hybrid *Dianthus caryophyllus.*
- *Commercial.*—Greenhouse carnation.

Form: Bush.
Height: Average.
Growth: Strong and upright with normal branching.
Foliage:
- *Quantity.*—Abundant.
- *Number of leaves.*—Depending on season.
- *Size of leaf.*—Medium.
- *Shape.*—Oblong.

- *Color.*—Upper side and under side — Blue/Green with waxy layer.

THE BUD

Size: Medium.
- *Diameter.*—About 1.5 cm.
- *Length.*—About 3 cm.

Shape: Cylindrical.
Color: When petals begin to unfurl — R.H.S. 41B.
Sepals:
- *Character.*—Sepals curl back as the flower opens.
- *Color.*—Inside and Outside — Grey/Green.

Calyx:
- *Size.*—Medium.
- *Aspect.*—Smooth.
- *Splitting.*—The calyx hardly ever splits.

THE FLOWER

Blooming habit: Continuous.
Size of bloom: Medium.
- *Diameter.*—About 8 cm.
- *Depth.*—About 4 cm.

Shape: High centered.
Petalage: Approximately 50 to 60 in number.
- *Arrangement.*—Imbricated.
- *Texture.*—Soft.
- *Appearance.*—Shiny.
- *Color.*—All petals: Top side and reverse side for all seasons — R.H.S. 41B.

Flower stem:
- *Length.*—Depends on season.
- *Color.*—Dark Green.
- *Character.*—Strong and upright.

Persistence: Flowers hang on and dry.
Fragrance: The flower is slightly fragrant.
Disease resistance: Resistant to fusarium oxysporum as observed at Aalsmeer.
Lasting quality:
- *On plant.*—20 Days.
- *As cut flower.*—10 To 15 days.

REPRODUCTIVE ORGANS

Stamens:
- *Number.*—Medium.
- *Arrangement.*—Average.
- *Anthers.*—Size: Medium. Color: Cream.
- *Pollen.*—There is no pollen.

Pistils:

*Number.*—One.

*Style.*—Approximately 30 mm. long.

*Color.*—White/Cream.

This new chrysanthemum variety most nearly resembles the variety "Doranja". The new plant differs, however, in that its coloration is quite new and also, it is less susceptible to fusarium oxysporum.

I claim:

1. A new and distinct carnation cultivar, substantially as herein shown and described, characterized by its continuous production of relatively large and solid light red flowers and by its ability to retain the same flower color production through all seasons.

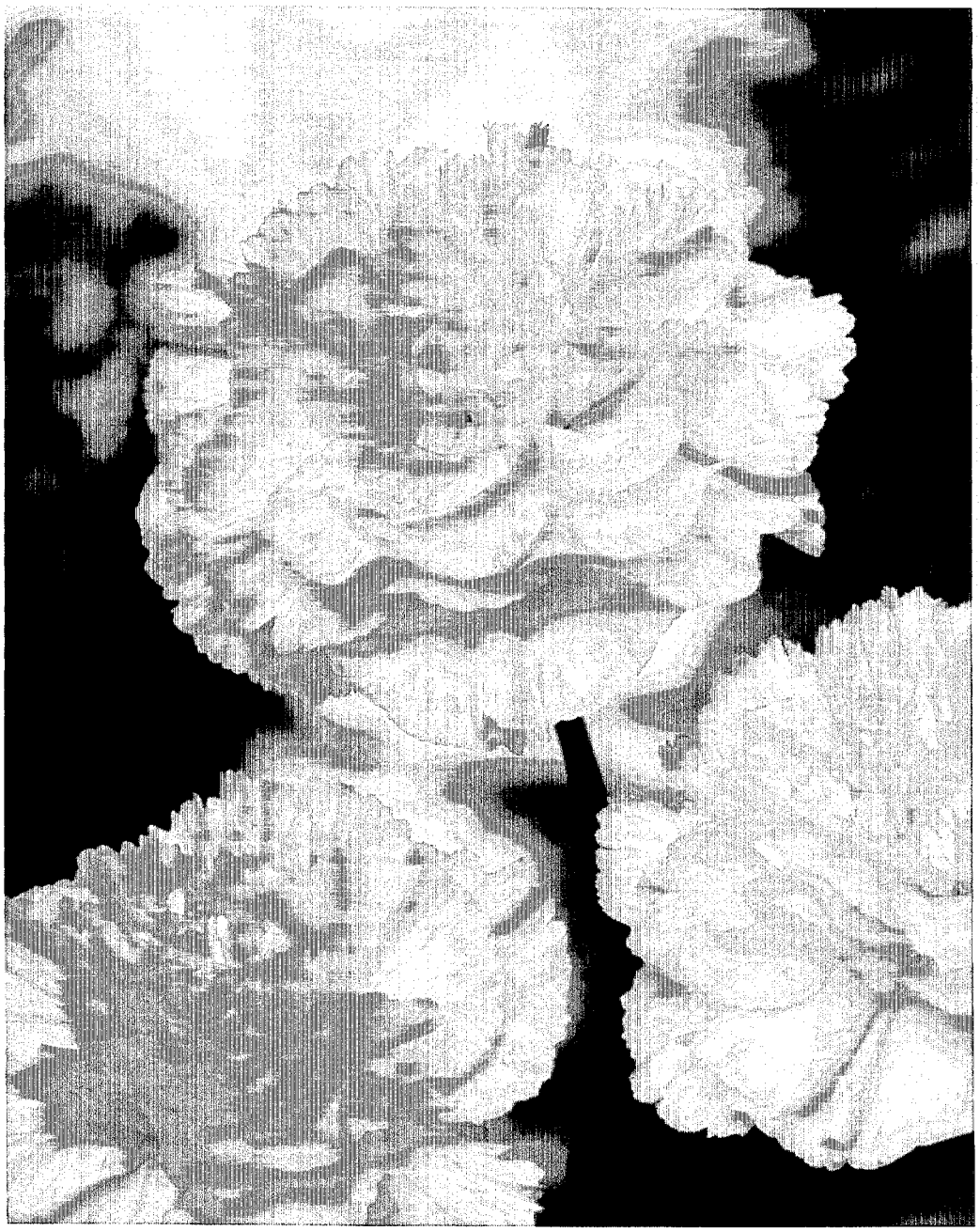

* * * * *